United States Patent
Kudo et al.

(10) Patent No.: US 9,282,932 B2
(45) Date of Patent: Mar. 15, 2016

(54) BIOMETRIC APPARATUS AND IMAGE-GENERATING METHOD

(75) Inventors: Hiroyuki Kudo, Tsukuba (JP); Naoya Saito, Tsukuba (JP); Yukio Ueda, Hamamatsu (JP); Kenji Yoshimoto, Hamamatsu (JP); Yutaka Yamashita, Hamamatsu (JP)

(73) Assignee: HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 177 days.

(21) Appl. No.: 14/130,690

(22) PCT Filed: Jun. 28, 2012

(86) PCT No.: PCT/JP2012/066552
§ 371 (c)(1),
(2), (4) Date: Feb. 3, 2014

(87) PCT Pub. No.: WO2013/005635
PCT Pub. Date: Jan. 10, 2013

(65) Prior Publication Data
US 2014/0135620 A1 May 15, 2014

(30) Foreign Application Priority Data
Jul. 7, 2011 (JP) ................. 2011-151086

(51) Int. Cl.
*A61B 5/00* (2006.01)
*A61B 10/00* (2006.01)
(Continued)

(52) U.S. Cl.
CPC ............. *A61B 5/7203* (2013.01); *A61B 5/0073* (2013.01); *A61B 5/0082* (2013.01);
(Continued)

(58) Field of Classification Search
CPC ............. A61B 10/0041; A61B 5/0073; A61B 5/0082; A61B 5/7203; A61B 6/5247; A61B 8/15; A61B 8/5207; G01N 21/4795; G06T 11/006
See application file for complete search history.

(56) References Cited

U.S. PATENT DOCUMENTS

| 4,662,222 A | 5/1987 | Johnson |
| 5,694,938 A | 12/1997 | Feng et al. |

(Continued)

FOREIGN PATENT DOCUMENTS

| CN | 101509871 | 8/2009 |
| CN | 101960296 | 1/2011 |

(Continued)

OTHER PUBLICATIONS

Yukio Ueda et al., "Three-dimensional imaging of a tissuelike phontom by diffusion optical tomography," Applied Optics, Dec. 1, 2001, pp. 6349-6355, vol. 40, No. 34.

(Continued)

*Primary Examiner* — Mark Remaly
(74) *Attorney, Agent, or Firm* — Drinker Biddle & Reath LLP

(57) ABSTRACT

The bioinstrumentation apparatus includes a light irradiation unit irradiating a measurement region with light, a light detection unit detecting diffused light from the measurement region, and a computing unit generating a reconstructed image for the interior of the measurement region. The computing unit calculates J coefficients $w_j$ set for every pixel of the reconstructed image and more than 0 and not more than 1 (where J is the number of pixels of the reconstructed image) and carries out successive approximation computation by the following iterative formula $$x_j^{(k+1)} = x_j^{(k)} + w_j d_j^{(k)}$$

(where k is an integer from 1 to N, N is the number of times of iterative computation, $x_j^{(k)}$ is a pixel value of the jth pixel on the kth iterative computation, and $d_j^{(k)}$ is an update amount of the jth pixel on the kth iterative computation) to generate the reconstructed image.

12 Claims, 17 Drawing Sheets

(51) Int. Cl.

| | | |
|---|---|---|
| *G06T 11/00* | (2006.01) | |
| *A61B 8/15* | (2006.01) | |
| *A61B 8/08* | (2006.01) | |
| *G01N 21/47* | (2006.01) | |
| *A61B 6/00* | (2006.01) | |

(52) U.S. Cl.
CPC ........... *A61B10/0041* (2013.01); *G06T 11/006* (2013.01); *A61B 6/5247* (2013.01); *A61B 8/15* (2013.01); *A61B 8/5207* (2013.01); *G01N 21/4795* (2013.01)

(56) References Cited

U.S. PATENT DOCUMENTS

| 5,905,261 | A | 5/1999 | Schotland et al. |
|---|---|---|---|
| 2008/0154126 | A1 | 6/2008 | Culver et al. |
| 2008/0260647 | A1 | 10/2008 | Intes et al. |

FOREIGN PATENT DOCUMENTS

| JP | 2001-264245 A | 9/2001 |
|---|---|---|
| JP | 2009-516561 A | 4/2009 |
| JP | 2010-094500 A | 4/2010 |
| JP | 2010-514478 A | 5/2010 |
| JP | 2011-505954 A | 3/2011 |
| JP | 2011-153976 | 8/2011 |
| TW | 201012303 | 3/2010 |
| WO | WO 2009/077947 | 6/2009 |
| WO | WO-2010/143421 A1 | 12/2010 |

OTHER PUBLICATIONS

Yukio Ueda et al., "Reflectance Diffuse Optical Tomography: Its Application to Human Brain Mapping," Japanese Journal of Applied Physics, 2005, pp. L1203-L1206, vol. 44, No. 38.

Richard J. Gaudette et al., "A comparison study of linear reconstruction techniques for diffuse optical tomographic imaging of absorption coefficient", Physics in Medicine and Biology, vol. 45, No. 4, Apr. 1, 2000, p. 1051-p. 1070, XP055169613.

| Numerical simulation algorithm | Runge-Kutta method |
|---|---|
| Image size | 132×132 |
| Spatial grid size | 1[mm] |
| Time step size | 0.25[ps] |
| Hot spot value | 0.020[cm$^{-1}$] |
| Hot spot diameter | 8[mm] |
| Back ground value | 0.010[cm$^{-1}$] |

*Fig.5*

| Image size | 66×66 |
|---|---|
| Spatial grid size | 2[mm] |
| Time step size | 1[ps] |
| The number of data | 32400 |
| Subset | 10 |
| Fixed iteration | 20000 |

| PRESENT EMBODIMENT | 0.87433 |
|---|---|
| CONVENTIONAL METHOD | 1.39214 |

BIOMETRIC APPARATUS AND IMAGE-GENERATING METHOD

TECHNICAL FIELD

The present invention relates to a bioinstrumentation apparatus and an image generating method.

BACKGROUND ART

As an apparatus for non-invasively measuring internal information of a living body such as the head and the breast, there has been proposed an apparatus which makes use of light absorbing characteristics of a living body to obtain the internal information, that is, an apparatus which uses what-is-called diffuse optical tomography (DOT). With such a measuring apparatus, a region of a living body to be measured is irradiated with light from a predetermined irradiation position, light which is propagated while being scattered in an interior of the region is detected at a predetermined detection position, and internal information on the region, that is, information on a light absorbing body such as a tumor etc. present in the interior of the region can be obtained from measured results of intensity, time waveform, etc. It is noted that Patent Document 1 has described a method for measuring a living body by diffuse optical tomography. Further, Non-Patent Documents 1 and 2 have described a method for reconstructing an image by successive approximation based on diffuse optical tomography.

CITATION LIST

Patent Literature

Patent Document 1: Japanese Patent Application Laid-Open No. 2001-264245

Non Patent Literature

Non-Patent Document 1: Y. Ueda, K. Ohta, M. Oda, M. Miwa, Y. Tsuchiya, and Y. Yamashita, "Three-dimensional imaging of a tissuelike phantom by diffusion optical tomography", Applied Optics Vol. 40 No. 34, pp. 6349-6355 (2001)

Non-Patent Document 2: Y. Ueda, T. Yamanaka, D. Yamashita, T. Suzuki, E. Ohmae, M. Oda and Y. Yamashita, "Reflectance Diffuse Optical Tomography: Its Application to Human Brain Mapping", Japanese Journal of Applied Physics Vol. 44 No. 38, pp. L1203-L1206 (2005)

SUMMARY OF INVENTION

Technical Problem

On measurement of a living body by diffuse optical tomography, spatial resolution and noise characteristics vary depending on a position inside a measurement region, thus resulting in generation of a non-uniform image. FIG. 17 is a schematic view for explaining such a phenomenon, showing a measurement region 100, and a light irradiation unit 101 and a light detection unit 102 installed on the surface of the measurement region 100. Inside the measurement region 100, the shorter the flight time of photons from emission from the light irradiation position 101 to arrival at the light detection position 102 becomes, the shorter the flight distance becomes and a flight path is restricted. In contrast, the longer the flight time of photons becomes, the longer the flight distance becomes and a flight path is not restricted. Then, data on a short flight time of photons includes a region A1 shown in FIG. 17, that is, many flight paths R1 passing through a region close to the surface of the measurement region. Further, data on a long flight time of photons includes a region A2 shown in FIG. 17, that is, many flight paths R2 passing through a region distant from the surface of the measurement region. Therefore, the amount of information in the region distant from the surface of the measurement region is less than the amount of information in the region close to the surface of the measurement region. As a result, spatial resolution and noise of the region distant from the surface of the measurement region are greater than spatial resolution and noise of the region close to the surface of the measurement region.

The present invention has been made in view of the above problem, and an object thereof is to provide a bioinstrumentation apparatus and an image generating method which are capable of suppressing a difference in spatial resolution and noise characteristics depending on a position inside a measurement region to generate an image which is uniform to a greater extent.

Solution to Problem

In order to solve the above-described problem, a first bioinstrumentation apparatus according to the present invention includes a light irradiation unit irradiating a measurement region of a subject with light, a light detection unit detecting diffused light from the measurement region, and a computing unit computing a light absorption coefficient distribution inside the measurement region on the basis of an output signal from the light detection unit to generate a reconstructed image for the interior of the measurement region, wherein the computing unit calculates J coefficients $w_j$ which are set for every pixel of the reconstructed image and more than 0 and not more than 1 (where an index j is an integer from 1 to J, and J is the number of pixels of the reconstructed image), and carries out successive approximation computation by means of the following iterative formula

[Formula 1]

$$x_j^{(k+1)} = x_j^{(k)} + w_j d_j^{(k)} \quad (1)$$

(where k is an integer from 1 to N, N is the number of times for carrying out iterative computation, $x_j^{(k)}$ is a pixel value of the jth pixel on the kth iterative computation, and $d_j^{(k)}$ is an update amount of the jth pixel on the kth iterative computation), thereby generating the reconstructed image.

Further, a second bioinstrumentation apparatus according to the present invention includes an irradiation unit irradiating a measurement region of a subject with radiation rays or sonic waves, a detection unit detecting the radiation rays or the sonic waves diffused from the measurement region, and a computing unit computing a radiation ray or sonic wave absorption coefficient distribution inside the measurement region on the basis of an output signal from the detection unit to generate a reconstructed image for the interior of the measurement region, wherein the computing unit calculates J coefficients $w_j$ which are set for every pixel of the reconstructed image and more than 0 and not more than 1 (where an index j is an integer from 1 to J, and J is the number of pixels of the reconstructed image), and carries out successive approximation computation by means of the above-described iterative formula (1), thereby generating the reconstructed image. It is noted that in the present invention, the radiation rays include short-wavelength electromagnetic waves, for example, X-rays, γ rays and microwaves, and the sonic waves include waves, for example, ultrasonic waves.

In the above-described bioinstrumentation apparatuses, J coefficients $w_1$ to $w_J$ set for each pixel in the reconstructed image are used to carry out successive approximation computation for reconstructing an image. For example, these coefficients $w_1$ to $w_J$ are set in such a manner that the convergence rate of the pixel concerned is in agreement with the region which is slowest in convergence rate on iterative computation carried out N times, and thereby, the convergence rate is made uniform to suppress a difference in spatial resolution and noise characteristics depending on a position inside the measurement region, thus making it possible to generate an image which is uniform to a greater extent.

Further, the bioinstrumentation apparatus may be configured so that the computing unit determines a convergence rate $C_N$ of a partial region which is slowest in convergence rate on iterative computation carried out N times (hereinafter referred to as a lowest convergence rate) among a plurality of partial regions in which the reconstructed image is divided and each of which contains a plurality of pixels, provides M values $v_m$ which meet a condition of $0 < v_m < 1$ (where m is an integer from 1 to M), carries out iterative computation N times for each m from 1 to M by means of the following iterative formula

[Formula 2]

$$x_j^{(k+1)} = x_j^{(k)} + v_m d_j^{(k)} \quad (2)$$

to calculate J pixel values $x_1^{(N)}$ to $x_J^{(N)}$ of each pixel, and sets a value $v_m$, when the convergence rate of each partial region obtained from the pixel values $x_1^{(N)}$ to $x_J^{(N)}$ is substantially in agreement with the lowest convergence rate $C_N$, as the coefficient $w_j$ for the plurality of pixels contained in the partial region. It is, thereby, possible to obtain the above-described effects more favorably.

The bioinstrumentation apparatus may also be configured so that the computing unit sets the coefficient $w_j$ of the partial region, which is slowest in convergence rate on iterative computation carried out N times, as 1. It is, thereby, possible to obtain the above-described effects more favorably.

A first image generating method according to the present invention is a method of irradiating a measurement region of a subject with light, detecting diffused light from the measurement region, and computing a light absorption coefficient distribution inside the measurement region on the basis of the detected signal to generate a reconstructed image for the interior of the measurement region, wherein the method calculates J coefficients $w_j$ which are set for every pixel of the reconstructed image and more than 0 and not more than 1 (where an index j is an integer from 1 to J, and J is the number of pixels of the reconstructed image), and carries out successive approximation computation by means of the following iterative formula

[Formula 3]

$$x_j^{(k+1)} = x_j^{(k)} + w_j d_j^{(k)} \quad (3)$$

(where k is an integer from 1 to N, N is the number of times for carrying out iterative computation, $x_j^{(k)}$ is a pixel value of the jth pixel on the kth iterative computation, and $d_j^{(k)}$ is an update amount of the jth pixel on the kth iterative computation), thereby generating the reconstructed image.

Further, a second image generating method according to the present invention is a method of irradiating a measurement region of a subject with radiation rays or sonic waves, detecting the radiation rays or the sonic waves diffused from the measurement region, and computing a radiation ray or sonic wave absorption coefficient distribution inside the measurement region on the basis of the detected signal to generate a reconstructed image for the interior of the measurement region, wherein the method calculates J coefficients $w_j$ which are set for every pixel of the reconstructed image and more than 0 and not more than 1 (where an index j is an integer from 1 to J, and J is the number of pixels of the reconstructed image), and carries out successive approximation computation by means of the above-described iterative formula (3), thereby generating the reconstructed image. It is noted that in the present invention, the radiation rays include short-wavelength electromagnetic waves, for example, X-rays, γ rays and microwaves, and the sonic waves include waves, for example, ultrasonic waves.

In the above-described image generating methods, J coefficients $w_1$ to $w_J$ set for every pixel in the reconstructed image are used to carry out successive approximation computation for reconstructing an image. For example, these coefficients $w_1$ to $w_J$ are set in such a manner that the convergence rate of the pixel concerned is in agreement with the region which is slowest in convergence rate on iterative computation carried out N times, and thereby, the convergence rate is made uniform to suppress a difference in spatial resolution and noise characteristics depending on a position inside the measurement region, thus making it possible to generate an image which is uniform to a greater extent.

Further, the image generating method may be configured so that the method determines a convergence rate $C_N$ of a partial region which is slowest in convergence rate on iterative computation carried out N times (hereinafter referred to as the lowest convergence rate) among a plurality of partial regions in which the reconstructed image is divided and each of which contains a plurality of pixels, provides M values $v_m$ which meet a condition of $0 < v_m < 1$ (where m is an integer from 1 to M), carries out iterative computation N times for each m from 1 to M by means of the following iterative formula

[Formula 4]

$$x_j^{(k+1)} = x_j^{(k)} + v_m d_j^{(k)} \quad (4)$$

to calculate J pixel values $x_1^{(N)}$ to $x_J^{(N)}$ of each pixel, and sets a value $v_m$, when the convergence rate of each partial region obtained from the pixel values $x_1^{(N)}$ to $x_J^{(N)}$ is substantially in agreement with the lowest convergence rate $C_N$, as the coefficient $w_j$ for the plurality of pixels contained in the partial region. It is, thereby, possible to obtain the above-described effects more favorably.

The image generating method may also be configured so that the method sets the coefficient $w_j$ of the partial region, which is slowest in convergence rate on iterative computation carried out N times, as 1. It is, thereby, possible to obtain the above-described effects more favorably.

Advantageous Effects of Invention

According to the bioinstrumentation apparatuses and image generating methods of the present invention, it is possible to suppress a difference in spatial resolution and noise characteristics depending on a position inside a measurement region, thereby generating an image which is uniform to a greater extent.

BRIEF DESCRIPTION OF DRAWINGS

FIG. 4 is a table showing conditions of a forward problem analysis when flight of photons inside a measurement region is simulated.

FIG. 5 is a table showing conditions of an inverse problem analysis when an image is reconstructed from a histogram of detected photons.

FIG. 16 is a table showing calculation results of standard deviation.

DESCRIPTION OF EMBODIMENTS

Hereinafter, a description will be given in detail of embodiments of a bioinstrumentation apparatus and an image generating method according to the present invention with reference to the accompanying drawings. In the description of the drawings, elements identical to each other are provided with the same reference symbols, and overlapping description will be omitted.

Figure 1:
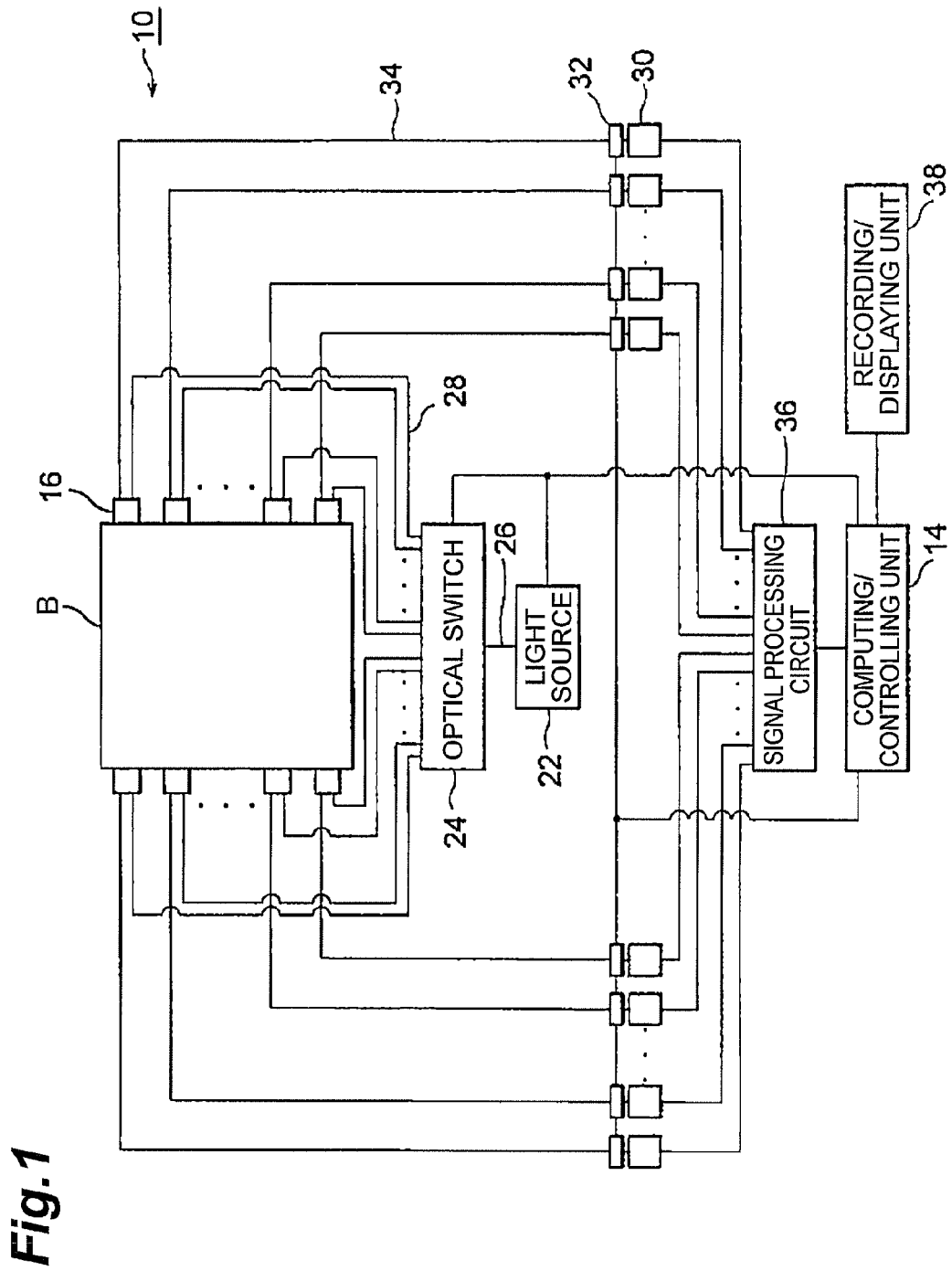
FIG. 1 is a drawing showing a configuration of a bioinstrumentation apparatus of one embodiment.

FIG. 1 is a drawing showing a configuration of a bioinstrumentation apparatus 10 according to one embodiment of the present invention. The bioinstrumentation apparatus 10 of the present embodiment is an apparatus which irradiates a measurement region B of a subject, that is, a measurement object, with light, detects diffused light (returned light) and estimates an average flight path of photons and an average optical path length on the basis of a detection position thereof and data on measured light intensity (for example, a time-resolved histogram of photons), thereby imaging information on an interior of the body as an image reconstructing problem. An image obtained by this apparatus is visualization of, for example, a position of a tumor, a distribution of oxygenated hemoglobin and deoxygenated hemoglobin, that is, a functional image of tissues of the body. It is noted that for example, the head and female breast etc. are assumed to be the measurement region B.

The bioinstrumentation apparatus 10 is provided with a light irradiation unit which irradiates the inside of the measurement region B with measurement light, a light detection unit which detects diffused light occurring from the measurement region B by irradiation of light from the light irradiation unit, and a computing unit 14 which calculates a spatial distribution of absorption coefficients of the measurement region B on the basis of an output signal from the light detection unit, thereby generating a reconstructed image of the measurement region B.

The light irradiation unit of the present embodiment is constituted with light emitting ends included respectively in n light emitting/detecting ends 16 installed on the measurement region B, a light source 22, and an optical switch 24. As the light source 22, for example, a laser diode can be used. A wavelength of the measurement light is preferably a wavelength of near infrared region which is approximately from 700 nm to 900 nm in view of a relationship between transmittance of a living body and an absorption coefficient of an absorbing body to be measured or others.

The measurement light is emitted from the light source 22, for example, as continuous light. The measurement light emitted from the light source 22 is irradiated from the light emitting/detecting ends 16 to the measurement region B. The optical switch 24 is an optical switch which outputs n for one input, inputs light from the light source 22 via a light source optical fiber 26, and successively provides the light to each of the n light emitting/detecting ends 16. That is, the optical switch 24 selects successively one by one the n emission optical fibers 28 connected respectively to the light emitting/detecting ends 16 and optically connects the emission optical fiber 28 with the light source 22.

The light detection unit of the present embodiment is constituted with light detecting ends included respectively in the above-described n light emitting/detecting ends 16, n photodetectors 30 corresponding respectively to the n light emitting/detecting ends 16, and n shutters 32 arranged at an input part front stage on each photodetector. Diffused light made incident into the light detecting end of each of the light emitting/detecting ends 16 from the measurement region B is input into each of the n photodetectors 30 via a detection optical fiber 34. The photodetector 30 generates an analog signal according to the light intensity of diffused light which has arrived at the corresponding light emitting/detecting end 16. As the photodetector 30, various elements can be used such as a photodiode, an avalanche photodiode, and a PIN photodiode, etc., in addition to a photomultiplier tube (PMT). In a case where the diffused light from the measurement region B is weak, a photodetector of high sensitivity or high gain is preferably used. A signal processing circuit 36 is connected to a signal output end of the photodetector 30, the signal processing circuit 36 performs A/D conversion of the analog signal output from the photodetector 30 to generate a digital signal that is in accordance with the light intensity of the diffused light, and provides the digital signal to the computing unit 14.

The computing unit 14 computes a light absorption coefficient distribution inside the measurement region B on the basis of the digital signal supplied from the signal processing circuit 36 to generate a reconstructed image for the interior of the measurement region B. The computing unit 14 is realized, for example, by a computer having computing means such as a CPU (central processing unit) and storage means such as a memory. It is preferable that the computing unit 14 additionally has functions of controlling light emission of the light source 22, operation of the optical switch 24, and opening/closing of the shutter 32. Also, the computing unit 14 is connected to a recording/displaying unit 38, thereby enabling visualization of the computation results by the computing unit 14, that is, a reconstructed image of the measurement region B.

Calculation of the internal information on the measurement region B, that is, the internal information measurement is performed, for example, as follows. The inside of the measurement region B is successively irradiated with measurement light from each of the n light emitting/detecting ends 16 to detect light diffused through the measurement region B by the n photodetectors 30 via the n light emitting/detecting ends 16. A spatial distribution of absorption coefficients inside the measurement region B is computed on the basis of the detection results, thereby generating a reconstructed image which includes information (internal information) on a position and shape of an absorbing body such as a tumor.

A known method which has been described in detail, for example, in Patent Document 1 may be preferably used in calculating a distribution of absorption coefficients in the computing unit 14.

Next, a description will be given for a method of generating a reconstructed image on the basis of a spatial distribution of light absorption coefficients. It is noted that the computation described hereinafter will be carried out by the computing unit 14. Here, in order to formulate an image reconstructing problem in diffuse optical tomography, values of respective pixels which constitute a reconstructed image on the basis of an unknown light absorption coefficient distribution are expressed by the following J-dimensional column vector x.

$$x=(x_1,x_2,\ldots,x_J)^T$$

Further, a photon histogram which is measurement data detected by the light detection unit is expressed by the following I-dimensional column vector T.

$$T=(T_1,T_2,\ldots,T_I)^T$$

Still further, an I×J type system matrix L which interrelates x with T is defined as follows.

$$L=\{l_{ij}\}$$

$l_i$ is given as an element vector of ith row of L. Further, an image in which a light absorption coefficient distribution is known and uniform is given as a J-dimensional column vector $x_{ref}$, and a photon histogram which is measurement data corresponding to the $x_{ref}$ is expressed by the following I-dimensional column vector B.

$$B=(B_1,B_2,\ldots,B_I)^T$$

Where the photon histogram which is the measurement data is free of statistical noise, the following formula (5) is held.

[Formula 5]

$$T_i=B_i\exp\{-l_i\cdot(x-x_{ref})\} \quad (5)$$

However, where statistical noise is interfused, the above formula (5) is not held. Therefore, it is necessary to determine an optimal x in a state that the statistical noise is interfused. Thus, in the present embodiment, what-is-called a maximum likelihood estimation method is used to determine the above-described x. In the maximum likelihood estimation method, a likelihood function is formulated from a detection probability of photons in the light detection unit, and an optimization problem is solved by means of the likelihood function as an objective function, thus making it possible to determine the optimal x.

A detection probability of photons in diffuse optical tomography is in accordance with the Poisson distribution, and the statistical noise thereof is also in accordance with the Poisson distribution. Therefore, the optimization problem of diffuse optical tomography is expressed by the following formula (6).

[Formula 6]

$$\text{maximize } F(x) \; s.t. \; x \geq 0 \quad (6)$$

Further, an objective function F (x) in the formula (6) is expressed by a log likelihood function shown in the following formula (7).

[Formula 7]

$$F(x) = -\sum_{i=1}^{I}\{B_i\exp(-l_i\cdot(x-x_{ref})) + T_i\exp(l_i\cdot x)\} \quad (7)$$

In the present embodiment, an OS-Convex algorithm is used to solve a maximization problem of the above formula (6) with a gradient method, thereby reconstructing an image. In the OS-Convex method, measurement data is divided into partial data sets which are called subsets, and a solution is updated for each subset so as to increase an evaluation function corresponding to each subset. Since solutions are updated by the number of subsets in one iterative computation, a convergence rate is improved.

Here, k is defined as an integer from 1 to N (N is the number of times of iterative computation), the number of subsets is defined as Q, q is defined as an integer from 1 to Q, and data set of the qth subset is defined as Sq. A specific iterative formula of the OS-Convex algorithm is expressed by the following formulas (8) and (9).

[Formula 8]

$$x_j^{(k,0)} = x_j^{(k,Q)} \quad (8)$$

[Formula 9]

$$x_j^{(k,q+1)} = x_j^{(k,q)} + x_j^{(k,q)}\frac{\sum_{i\in S_q}l_{ij}\{B_i\exp(-l_i\cdot(x-x_{ref}))-T_i\}}{\sum_{i\in S_q}l_{ij}(l_i\cdot x)B_i\exp(-l_i\cdot(x-x_{ref}))} \quad (9)$$

Here, an iterative formula which is generally used in a method of successive approximation is shown in the following formula (10). According to this iterative formula, the (k+1)th value $x_j^{(k+1)}$ is a sum of the kth value $x_j^{(k)}$ and an update amount $d_j^{(k)}$.

[Formula 10]

$$x_j^{(k+1)}=x_j^{(k)}+d_j^{(k)} \quad (10)$$

It is noted that in the above-described OS-Convex algorithm, the update amount $d_j^{(k)}$ is expressed as shown in the following formula (11).

[Formula 11]

$$d_j^{(k,q)} = x_j^{(k,q)} \frac{\sum_{i \in S_q} l_{ij}\{B_i \exp(-I_i \cdot (x - x_{ref})) - T_i\}}{\sum_{i \in S_q} l_{ij}(I_i \cdot x) B_i \exp(-I_i \cdot (x - x_{ref}))} \quad (11)$$

A pixel having a fast convergence (convergence rate) of solution is large in value of the update amounts $d_j^{(1)}$ to $d_j^{(N)}$ obtained respectively in iterative computation carried out N times. On the other hand, a pixel having a slow convergence rate is small in value of the update amounts $d_j^{(1)}$ to $d_j^{(N)}$ obtained respectively in iterative computation carried out N times. Therefore, when convergence rates of two pixels which should be basically equal in value are different from each other, respective values after iterative computation carried out certain times are consequently different from each other. That is, where there is a large difference in the convergence rate for every pixel, there will be deterioration in uniformity of spatial resolution in a reconstructed image.

That is, convergence rates of values $x_1^{(N)}$ to $x_J^{(N)}$ of J pixels are brought closer to each other, thus making it possible to make uniform the spatial resolution (image quality) of a reconstructed image after iterative computation is carried out N times. Accordingly, an update amount $d_j^{(k)}$ in the above formula (10) may be multiplied by arbitrary coefficient which is different for every pixel in such a manner that the convergence rates of values $x_1^{(N)}$ to $x_J^{(N)}$ are brought closer to each other (preferably, they are approximately equal). However, the update amount $d_j^{(k)}$ is a maximum update amount which increases an evaluation function of the jth pixel, and therefore, when an update amount $d_j^{(k)}$ of a pixel slow in convergence rate is multiplied by a coefficient greater than 1, the evaluation function is not increased but decreased, which is not favorable. Thus, an update amount $d_j^{(k)}$ of a pixel fast in convergence rate is multiplied by a coefficient smaller than 1, thus making it possible to increase the evaluation function and also adjust a convergence rate in conformity with the pixel slow in convergence rate. In other words, a coefficient $w_j$ (hereinafter, referred to as a step size) which meets the following formula (12) is set for every pixel and the update amount $d_j^{(k)}$ is multiplied by the step size $w_j$, thus making it possible to control a convergence rate of each pixel value $x_1^{(N)}$ to $x_J^{(N)}$ in an appropriate manner.

[Formula 12]

$$0 < w_j \leq 1 \quad (12)$$

Therefore, the above-described iterative computation formula (10) can be rewritten as the following formula (13).

[Formula 13]

$$x_j^{(k+1)} = x_j^{(k)} + w_j d_j^{(k)} \quad (13)$$

When, for example, the iterative computation formula shown in the above formula (13) is applied to the previously described OS-Convex algorithm, the iterative computation formula shown in the formula (9) is given as the following formula (14).

[Formula 14]

$$x_j^{(k,q+1)} = x_j^{(k,q)} + w_j x_j^{(k,q)} \frac{\sum_{i \in S_q} l_{ij}\{B_i \exp(-I_i \cdot (x - x_{ref})) - T_i\}}{\sum_{i \in S_q} l_{ij}(I_i \cdot x) B_i \exp(-I_i \cdot (x - x_{ref}))} \quad (14)$$

Next, a description will be given for a method of determining the step size $w_j$.

<Evaluation of Convergence Rate>

In order to determine the step size it is necessary to determine a convergence rate of each pixel on the basis of the measurement data, and thereafter judge the pixel which is slowest in convergence rate. A convergence rate of each pixel can be evaluated by a contrast recovery coefficient (CRC).

In diffuse optical tomography, mutually adjacent pixels are apt to be close in convergence rate. Therefore, in the present embodiment, an image is divided into a plurality of partial regions, each of which contains a plurality of pixels, a region which acts as a spot is disposed in each of the partial regions, and a CRC at the spot is used as a value corresponding to the convergence rate of the region thereof. It is noted that the CRC is defined by the following formula (15).

[Formula 15]

$$CRC = \frac{(SP_m^R - BG_m^R)/BG_m^R}{(SP_m^{Tr} - BG_m^{Tr})/BG_m^{Tr}} \quad (15)$$

Here, SP represents a pixel value at a spot region, and BG represents a pixel value outside the spot region (background region). Further, an index m represents an average value inside the region, an index R represents a pixel value after image reconstruction, and an index Tr represents a pixel value based on measurement data.

<Determination of Step Size $w_j$>

Figure 2:
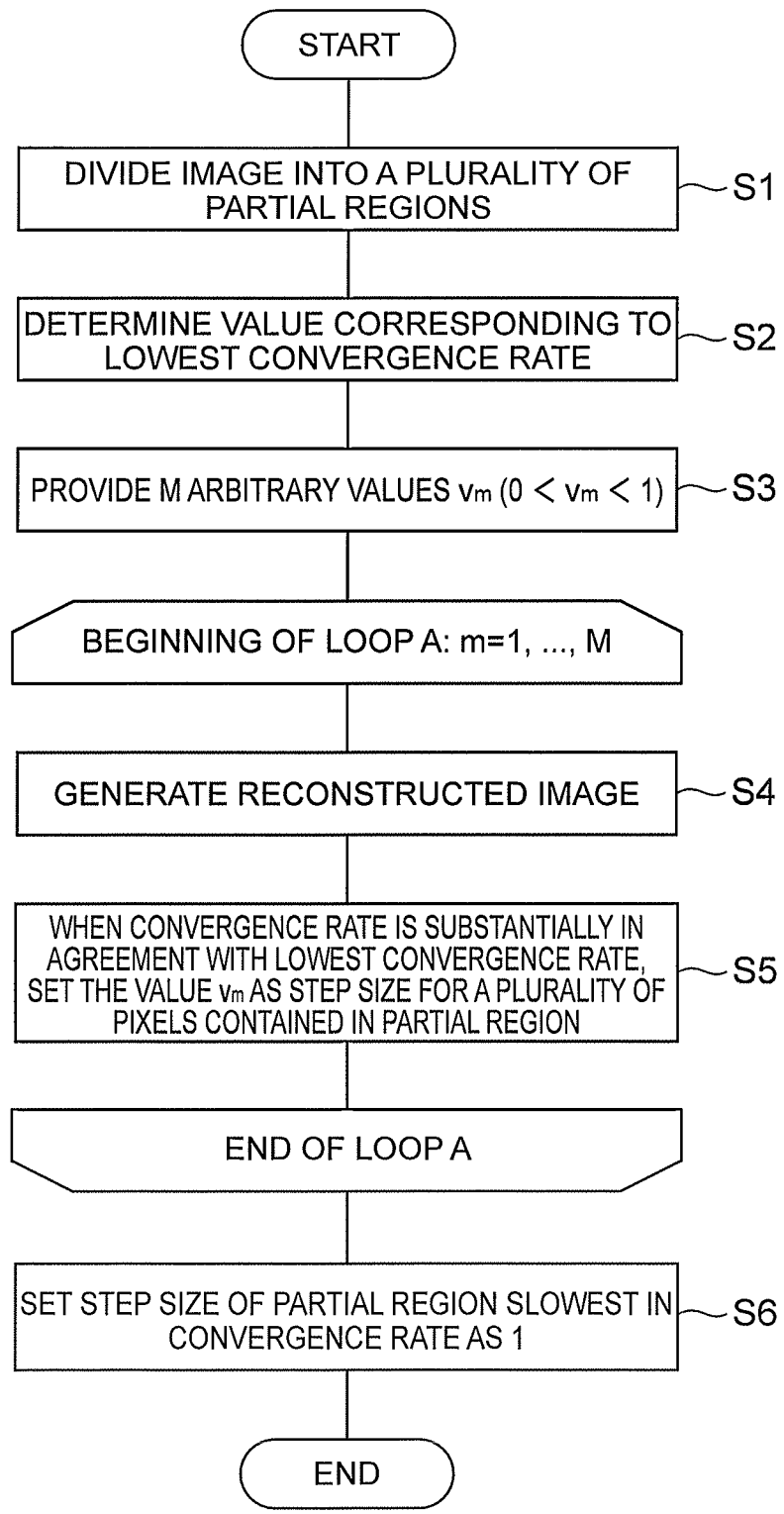
FIG. 2 is a flow chart showing a specific method for determining a coefficient (step size).

FIG. 2 is a flow chart showing a specific method for determining a step size $w_j$ on the basis of the above-described method for evaluating a convergence rate. In this method, first, an image is divided into E partial regions (Step S1). It is noted that in the following description, a pixel value set of any given partial region e is given as $R_e$.

Next, arbitrary iteration times of N is set, and the partial region which is smallest in CRC on iterative computation carried out N times (that is, the convergence rate is slowest) is determined to define the CRC as the lowest convergence rate $C_N$ (Step S2). Then, there are provided M arbitrary values $v_m$ which meet a condition of $0 < v_m < 1$ (where m is an integer from 1 to M, and $v_1$ to $v_m$ are mutually different values) (Step S3). It is noted that Step S3 may be carried out before Step S2 and Step S1.

Further, each m from 1 to M is subjected to iterative computation carried out N times by means of the following iterative formula (16) to calculate J pixel values $x_1^{(N)}$ to $x_J^{(N)}$ of each pixel, thereby generating a reconstructed image (Step S4).

[Formula 16]

$$x_j^{(k+1)} = x_j^{(k)} + v_m d_j^{(k)} \quad (16)$$

Then, where a convergence rate of a certain partial region obtained from the pixel values $x_1^{(N)}$ to $x_J^{(N)}$ is substantially in agreement with the lowest convergence rate $C_N$, the value $v_m$ obtained at that time is given as a step size $w_j$ of a plurality of pixels contained in the partial region (Step S5). Subsequently, the previously described Steps S4 and S5 are iterated M times, or Steps S4 and S5 are iterated until step sizes $w_j$ are determined for all partial regions excluding the partial region slowest in convergence rate.

Finally, the step size $w_j$ of the partial region slowest in convergence rate on iterative computation carried out N times is given as 1 (Step S6). As described so far, every pixel of all the partial regions is given a step size $w_j$.

A description will be given for effects obtained by the bioinstrumentation apparatus 10 and the image generating method of the present embodiment described above, with problems in a conventional method.

Diffuse optical tomography is an image reconstructing method using a diffusive flight path of near-infrared light inside a living body. When an image is reconstructed in diffuse optical tomography, a method for reconstructing the image by successive approximation is employed instead of an analytical method, however, an ordinary image reconstructing method by successive approximation such as a conjugate gradient method has a problem that a non-uniform image which varies greatly in spatial resolution and noise characteristics inside the reconstructed image is generated.

A reason for a non-uniformity of image quality is that in diffuse optical tomography, the amount of information contained in measurement data is significantly different depending on a position inside a measurement region. That is, in diffuse optical tomography using a time-resolved measurement method, photons made incident from a light incident end on the surface of the measurement region fly while being scattered iteratively inside the measurement region and are detected upon arrival at a light detecting end on the surface of the measurement region. The shorter the flight time of photons from incidence to detection is, the shorter the flight distance becomes and a flight path is thereby restricted. In contrast, the longer the flight time is, the longer the flight distance becomes and the flight path is thereby not restricted. Therefore, the amount of information contained in the measurement data varies depending on the flight time of photons. In a typical case, where the flight time of photons is short, the ratio of the flight path close to the surface of the measurement region is increased, and where the flight time is long, the ratio of the flight path distant from the surface of the measurement region (near the center of the measurement region) is increased. As a result, the amount of information near the center of the measurement region is less as compared with that near the surface thereof. Accordingly, the spatial resolution and noise at the periphery of a reconstructed image are greater than the spatial resolution and noise near the center of the reconstructed image, which causes variance in spatial resolution and noise inside the reconstructed image.

In the bioinstrumentation apparatus 10 and the image generating method of the present embodiment, J coefficients $w_1$ to $w_J$ set for respective pixels in a reconstructed image are used to perform successive approximation computation for reconstructing the image. Then, as described in the present embodiment, these coefficients $w_1$ to $w_J$ are set in such a manner that the convergence rate of the pixel concerned is in agreement with the partial region which is slowest in convergence rate on iterative computation carried out N times, and thereby, the convergence rate is made uniform to suppress a difference in spatial resolution and noise characteristics depending on a position inside the measurement region, thus making it possible to generate an image which is uniform to a greater extent.

Figure 3:
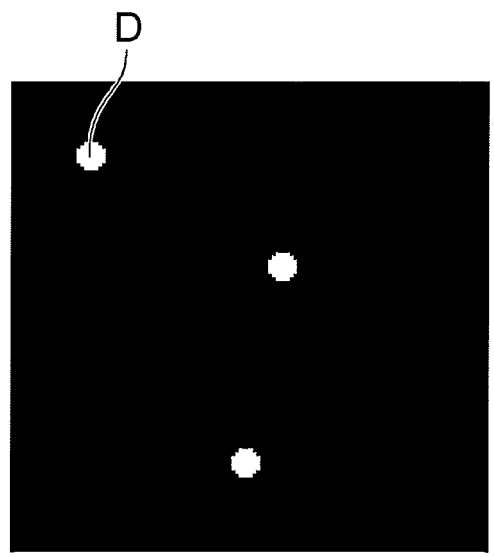
FIG. 3 is a drawing showing two types of measurement regions which are objects to be reconstructed in a simulation.
Figure 3:
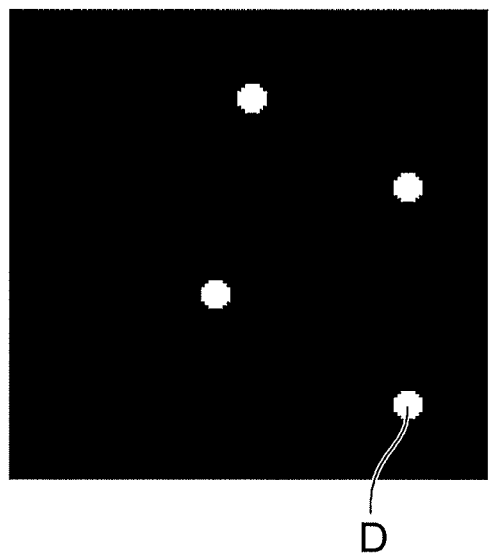

Here, a description will be given for results of a simulation conducted for confirming the above effects by the image generating method of the present embodiment. (a) in FIG. 3 and (b) in FIG. 3 are drawings which show two types of measurement regions to be reconstructed in this simulation. Each of the drawings shows a plurality of light absorbing objects D, for example, tumors. It is noted that the center coordinates (x, y) of three light absorbing objects D shown in (a) in FIG. 3 are respectively (21, 20), (64, 106), and (75, 51). Further, the center coordinates (x, y) of four light absorbing objects D shown in (b) in FIG. 3 are respectively (56, 79), (66, 24), (109, 49), and (109, 110).

In this simulation, the following Steps (1) to (3) were carried out.

(1) In order to evaluate a convergence rate of each pixel, image reconstruction was carried out at spots uniformly disposed inside an image, thereby determining step sizes $w_1$ to $w_J$.

(2) Obtained step sizes $w_1$ to $w_J$ were used to reconstruct the image, thereby confirming that spatial resolution was approximately uniform all over in the reconstructed image.

(3) Evaluation was made for propagation of noise between regions by reconstruction of a background image.

Conditions common to the above Steps (1) to (3) are as follows. First, FIG. 4 and FIG. 5 show respectively the conditions of two types of analyses, that is, a forward problem analysis which simulates flight of photons inside a measurement region, and an inverse problem analysis which reconstructs an image from a histogram of photons detected. As shown in FIG. 4 and FIG. 5, the forward problem analysis and the inverse problem analysis are mutually different in grid size and image size, due to conversion of a continuous system to a discrete system. Photons detected by the light detection unit are inevitably obtained as discrete data. On the other hand, values of numerical simulation are calculated in a form close to a continuous function. Therefore, in this simulation, down sampling is carried out to convert the continuous system to the discrete system.

(1) Determination of Step Sizes $w_1$ to $w_J$

Figure 6:
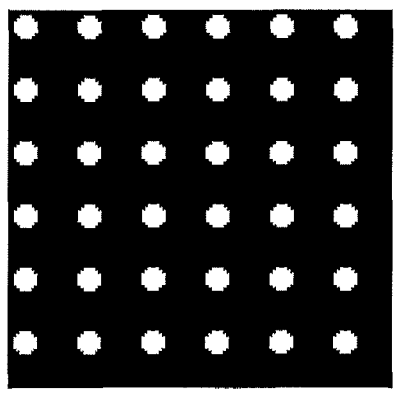
FIG. 6 is a drawing showing four images used in determining a step size on simulation.
Figure 6:
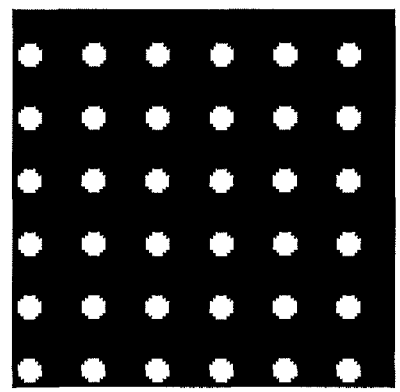
Figure 6:
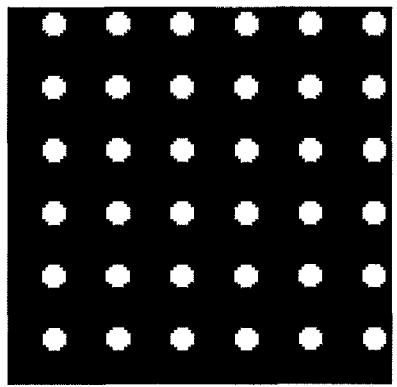
Figure 6:
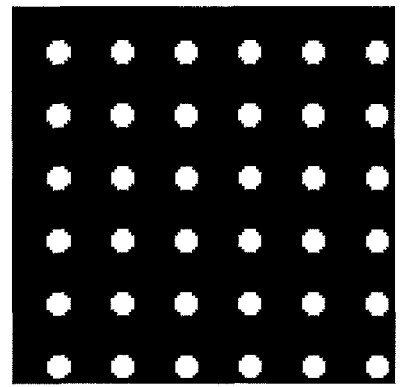

An image containing pixels of 132 rows and 132 columns on the basis of measurement data was divided into partial regions of 12 rows and 12 columns, and a hot spot was disposed at the center of each partial region. In this simulation, four images shown in (a) in FIG. 6 to (d) in FIG. 6 were reconstructed to determine a CRC of each partial region, thereby determining step sizes $w_1$ to $w_J$ of all the pixels by the previously described method.

(2) Reconstruction of Image

Next, the step sizes $w_1$ to $w_J$ determined in Step (1) were used to compute the iterative computation formula shown in the formula (14), thereby reconstructing an image. In this Step, if there is a difference in CRC of each partial region, an edge will appear in an image, and therefore, an image in which the step size $w_1$ to $w_J$ was given as each pixel value (step size image) was smoothed by using an averaging filter to obtain a step size image which was changed smoothly. In this simulation, an averaging filter used was with a kernel size of 9×9.

Figure 7:
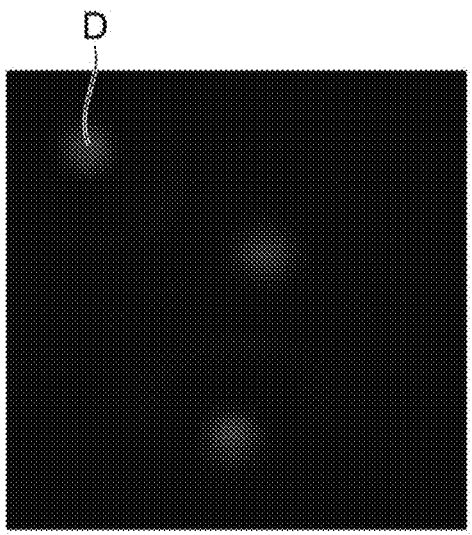
FIG. 7 includes (a) an image corresponding to the image shown in (a) in FIG. 3 and after reconstruction by simulation, and (b) an image corresponding to the image shown in (a) in FIG. 3 and after reconstruction by a conventional method using no step size.
Figure 7:
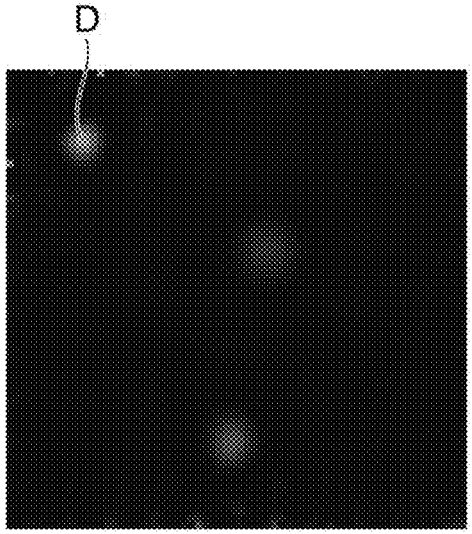
Figure 8:
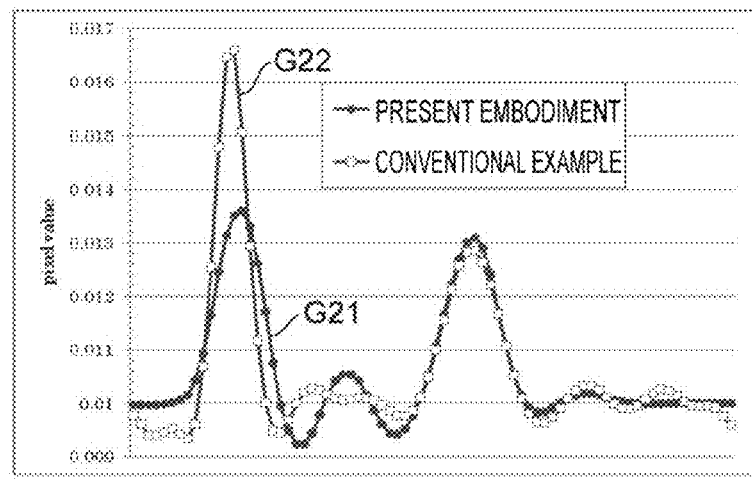
FIG. 8 includes graphs showing changes in pixel values on three lines shown in FIG. 9.
Figure 8:
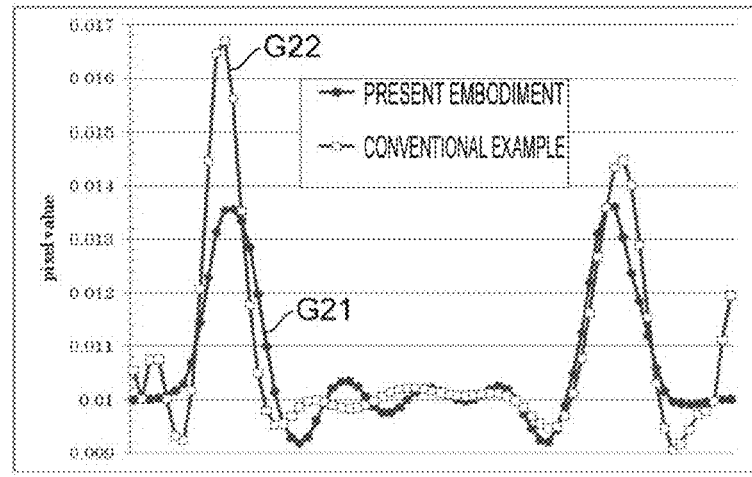
Figure 8:
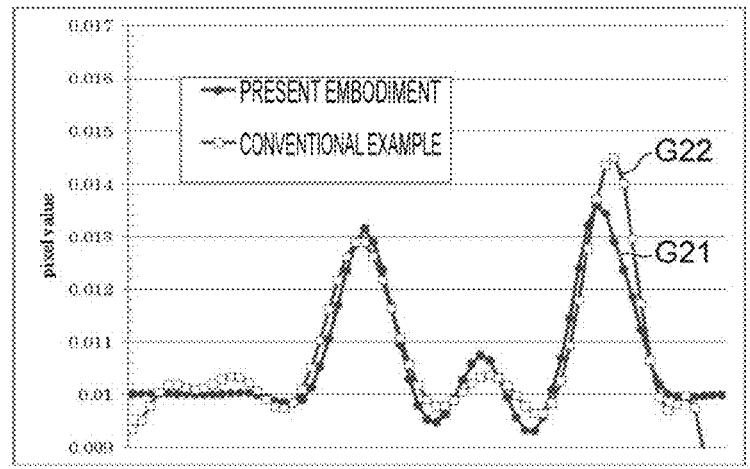
Figure 9:
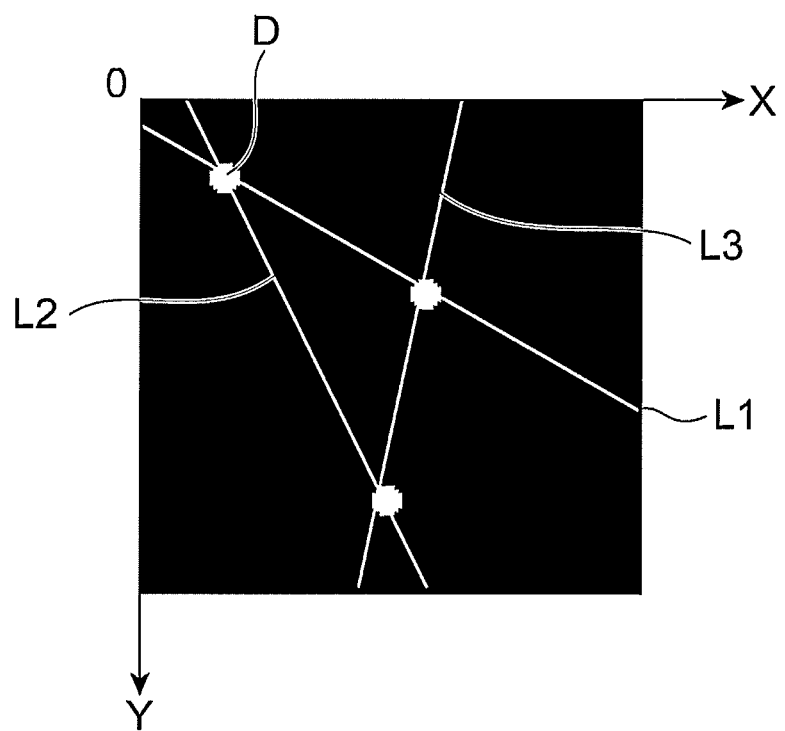
FIG. 9 is a drawing showing three lines assumed on the image.
Figure 10:
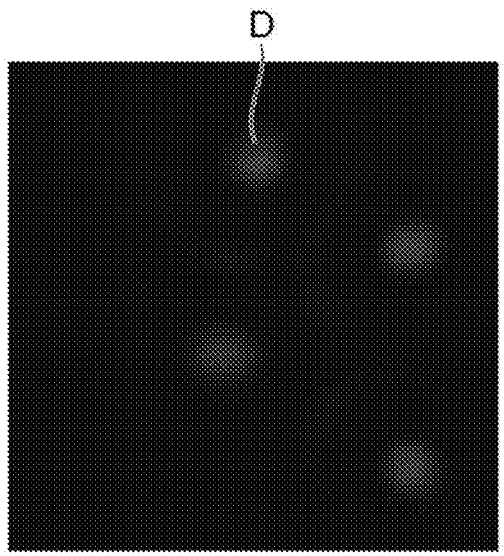
FIG. 10 includes (a) an image corresponding to the image shown in (b) in FIG. 3 and after reconstruction by simulation, and (b) an image corresponding to the image shown in (b) in FIG. 3 and after reconstruction by a conventional method using no step size.
Figure 10:
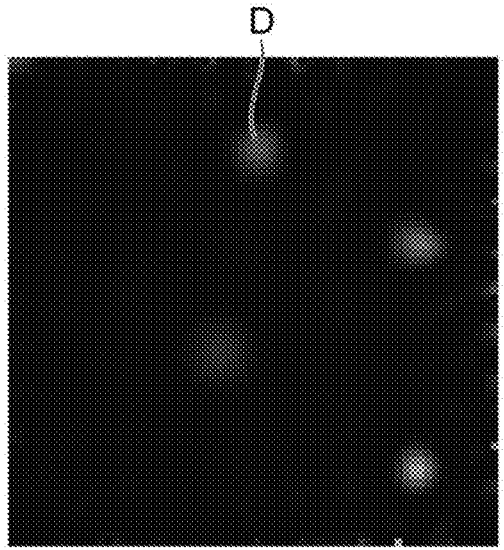
Figure 11:
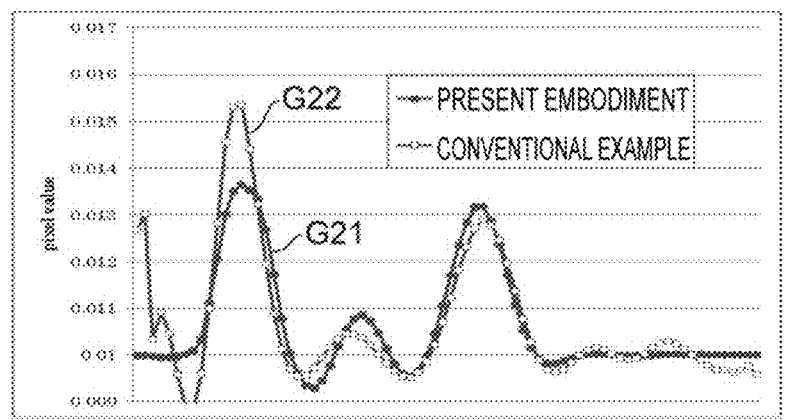
FIG. 11 includes graphs showing changes in pixel values on two lines shown in FIG. 12.
Figure 11:
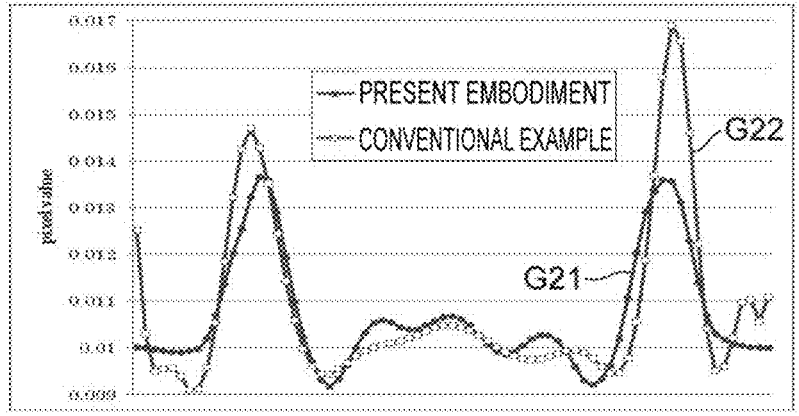
Figure 12:
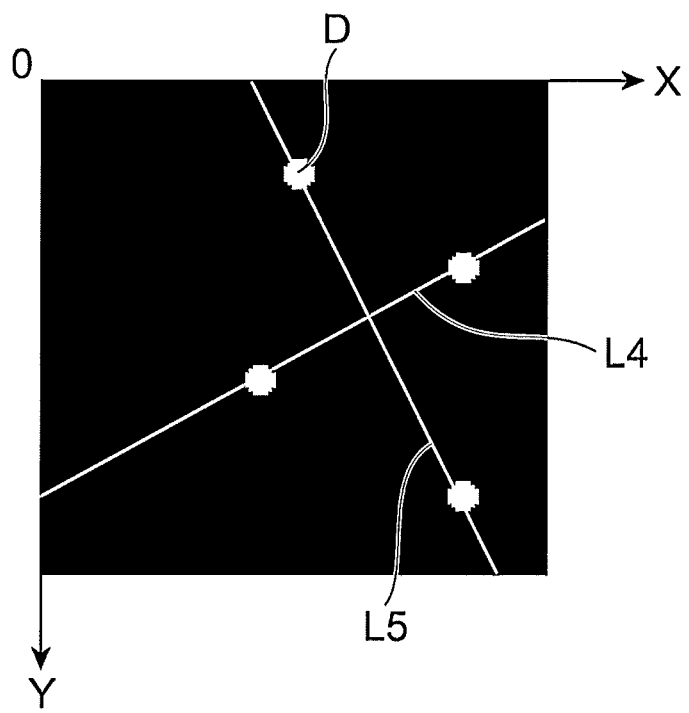
FIG. 12 is a drawing showing two lines assumed on the image.

(a) in FIG. 7 is an image corresponding to the image shown in (a) in FIG. 3 and after reconstruction by the present simulation. (b) in FIG. 7 is an image corresponding to the image shown in (a) in FIG. 3 and after reconstruction by a conventional method without step sizes $w_1$ to $w_J$. (a) in FIG. 8 to (c) in FIG. 8 are graphs which show changes in pixel value on three lines L1 to L3 passing through light absorbing objects D as shown in FIG. 9, graphs G21 show changes in pixel value by the present simulation, and graphs G22 show changes in pixel value by the conventional method. Further, (a) in FIG. 10 is an image corresponding to the image shown in (b) in FIG. 3 and after reconstruction by the present simulation. (b) in FIG. 10 is an image corresponding to the image shown in (b) in FIG. 3 and after reconstruction by a conventional method without step sizes $w_1$ to $w_J$. (a) in FIG. 11 and (b) in FIG. 11 are graphs showing changes in pixel value on two lines L4 and L5 passing through light absorbing objects D as shown in FIG. 12, graphs G21 show changes in pixel value by the present simulation, and graphs G22 show changes in pixel value by the conventional method.

With reference to (b) in FIG. 7, in the conventionally reconstructed image, it is found that a pixel value in the light absorbing object D is relatively high at the periphery of the image, for example, on the upper left side, which is significantly different from a pixel value in the light absorbing object D near the center of the image. In contrast, in the reconstructed image of the present embodiment using the step sizes $w_1$ to $w_J$, as shown in (a) in FIG. 7, a pixel value in each of the light absorbing objects D is substantially equal at the periphery and near the center of the image. Further, with reference to FIG. 8, in the conventionally reconstructed image, there is a large change in pixel value at the periphery of the image. In contrast, as shown in (a) in FIG. 8 to (c) in FIG. 8, in the reconstructed image of the present embodiment, there is a small change in pixel value at the periphery of the image. This is because of the fact that in the present embodiment, a step size $w_j$ is increased near the center of the image to increase an update amount on iterative computation, by which the step size $w_j$ is decreased at the periphery of the image to decrease the update amount accordingly. The above results clearly show that according to the bioinstrumentation apparatus 10 and the image generating method of the present embodiment, the convergence rate is made uniform to suppress a difference in spatial resolution depending on a position inside a measurement region, thereby generating an image which is uniform to a greater extent.

Figure 13:
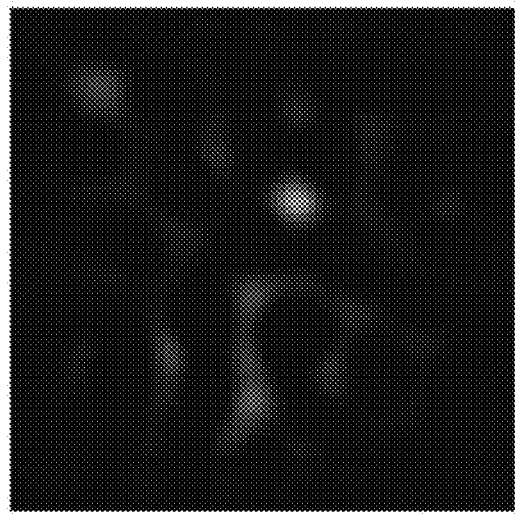
FIG. 13 includes (a) an image corresponding to the image shown in (a) in FIG. 3 and after reconstruction by the present embodiment with addition of statistical noise, and (b) an image corresponding to the image shown in (a) in FIG. 3 and after reconstruction by a conventional method with addition of statistical noise.
Figure 13:
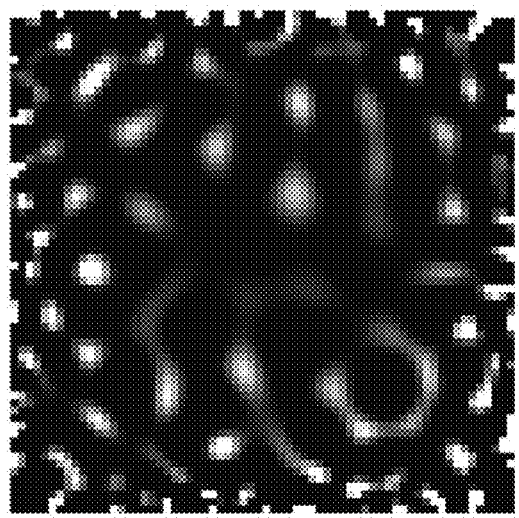
Figure 14:
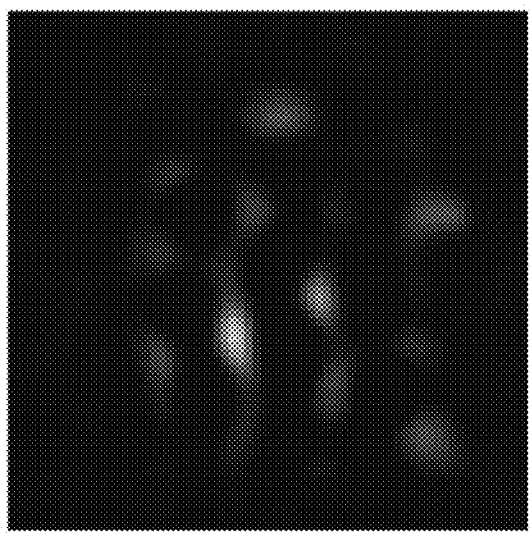
FIG. 14 includes (a) an image corresponding to the image shown in (b) in FIG. 3 and after reconstruction by the present embodiment with addition of statistical noise, and (b) an image corresponding to the image shown in (b) in FIG. 3 and after reconstruction by a conventional method with addition of statistical noise.
Figure 14:
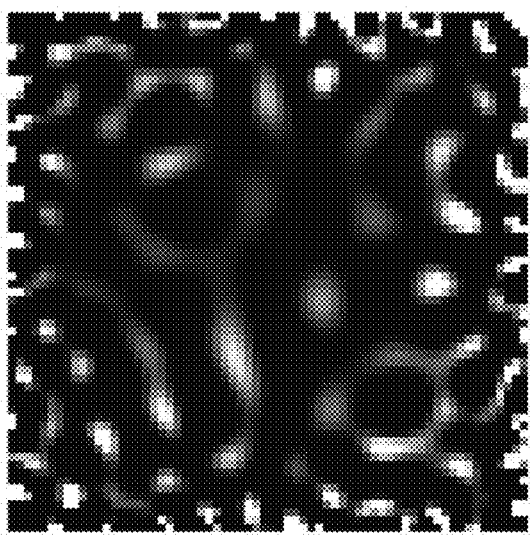

Next, results of a simulation where statistical noise is added, are shown. In this simulation, a photon histogram was subjected to fitting in such a manner that a maximum value of the respective detected photon histograms was given as a constant value (for example, 50) and, thereafter, Poisson noise was added to the photon histogram. (a) in FIG. 13 is an image corresponding to the image shown in (a) in FIG. 3 and after reconstruction by the present embodiment with addition of statistical noise. (b) in FIG. 13 is an image corresponding to the image shown in (a) in FIG. 3 and after reconstruction by a conventional method with addition of statistical noise. Further, (a) in FIG. 14 is an image corresponding to the image shown in (b) in FIG. 3 and after reconstruction by the present embodiment with addition of statistical noise. (b) in FIG. 14 is an image corresponding to the image shown in (b) in FIG. 3 and after reconstruction by the conventional method with addition of statistical noise.

With reference to (b) in FIG. 13 and (b) in FIG. 14, in the presence of statistical noise, the conventional method using no step sizes $w_1$ to $w_J$ exhibits a high spatial resolution at the periphery of the image to result in a significant influence of noise but does not exhibit a high spatial resolution near the center of the image and influence of noise is small. In contrast, with reference to (a) in FIG. 13 and (a) in FIG. 14, the method of the present embodiment which uses the step sizes $w_1$ to $w_J$, suppresses an update amount at the periphery of the image on iterative computation, thereby remarkably suppressing an influence of noise, and making it possible to observe clearly the shape of the light absorbing object D on the upper left side. On the other hand, the influence of noise is suppressed near the center of the image in a similar extent to the conventional method. Statistical noise near the center of the image is greater than statistical noise at the periphery of the image, due to a change in improving rate in resolution depending on the presence or absence of the statistical noise, and such a phenomenon is caused by the use of a step size which is determined on the assumption of no statistical noise.

As described above, where the measurement data contains statistical noise, the living body measuring method of the present embodiment shows a change in pixel value, compared with the conventional method, however, no significant change is found in morphological characteristics of statistical noise in an image as a whole. That is, according to the living body measuring method of the present embodiment, it is possible to selectively delay the improvement in resolution at the periphery of the image.

Figure 15:
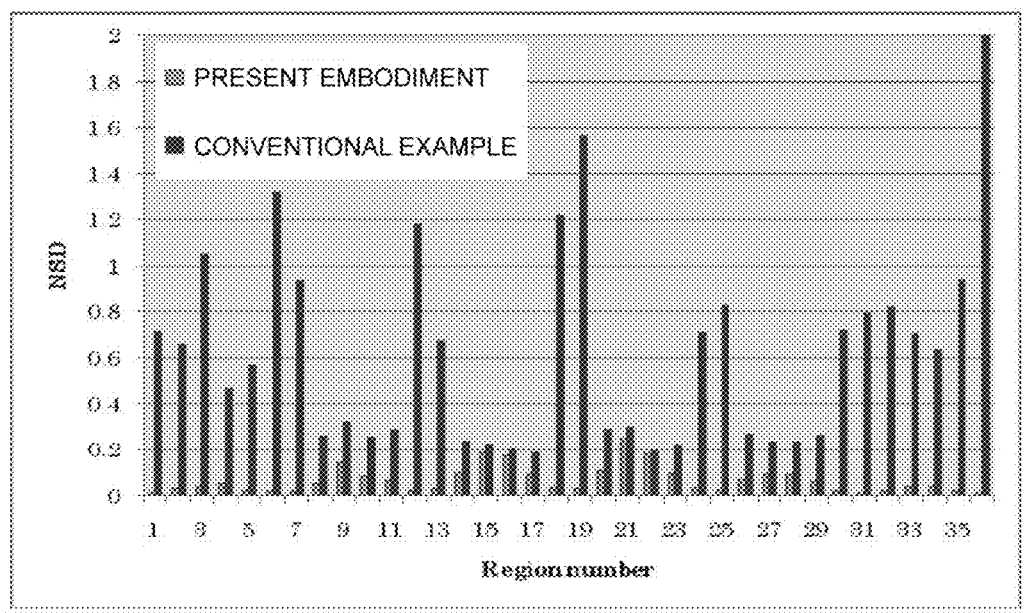
FIG. 15 is a graph showing NSD for every partial region.
Figure 17:
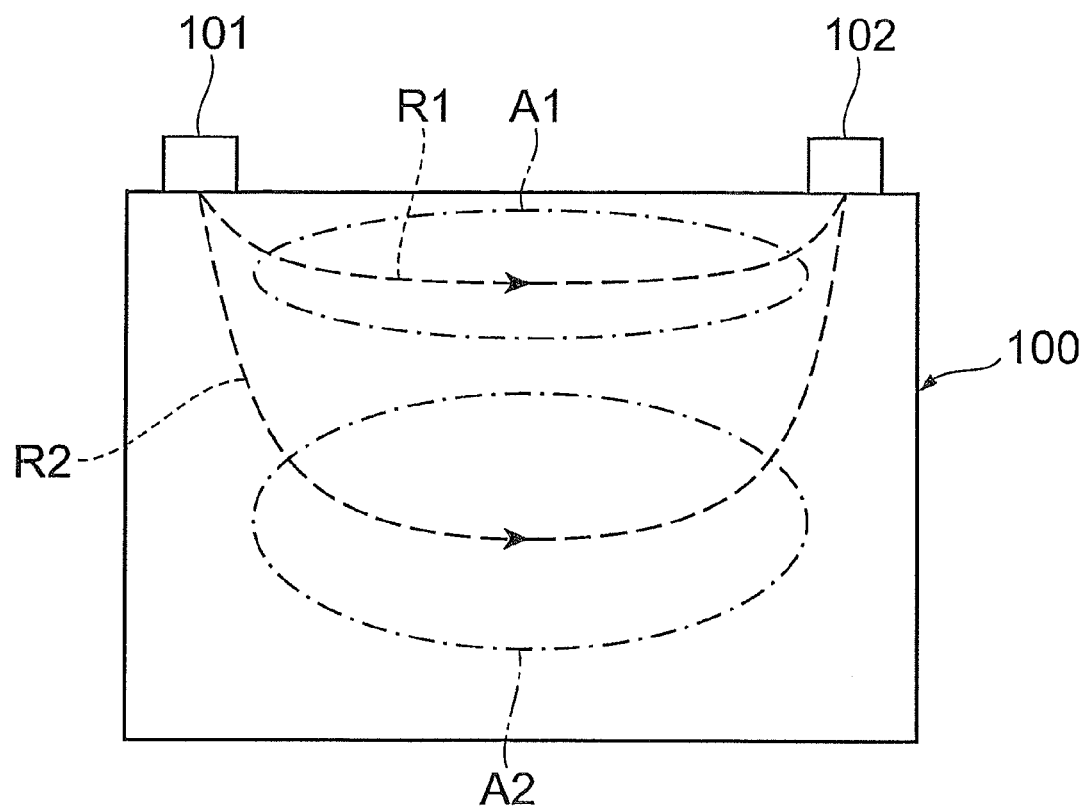
FIG. 17 is a schematic view for explaining a phenomenon in which a non-uniform image is generated in diffuse optical tomography.

Subsequently, a description will be given for evaluation of noise on a background image where no light absorbing object D is disposed. Here, Poisson noise was added to measurement data free of the light absorbing object D. A reconstructed image obtained at this time is an image deformed by noise. The reconstructed image was divided into 36 partial regions of 6 rows and 6 columns, and given numbers successively from the upper left side to the lower right side. Thereafter, each of the partial regions was evaluated by referring to a noise index (NSD: Normalized Standard Deviation). It is noted that NSD is calculated by the following formula (17). Further, FIG. 15 is a graph showing NSD of each partial region, and the horizontal axis indicates partial region numbers and the vertical axis indicates NSD values. It is noted that an index SD means standard deviation.

[Formula 17]

$$NSD = BG_{SD}^R / BG_m^R \qquad (17)$$

Further, a standard deviation is calculated in which NSD of each partial region is a population, and the standard deviation is used as a value for evaluating non-uniformity of noise between partial regions. FIG. 16 is a table showing computation results of the standard deviation.

With reference to FIG. 15, it is apparent that there is a significant variance in NSD between partial regions in the conventional method. In contrast, a variance in NSD is in general suppressed in the method of the present embodiment. From this finding, it is also apparent that in the method of the present embodiment, a step size $w_j$ used in bringing spatial resolution close to uniformity also alleviates non-uniformity of noise propagation. Further, as shown in FIG. 16, the non-uniformity of noise is also decreased by the method of the present embodiment compared with the conventional method.

The bioinstrumentation apparatus and the image generating method of the present invention shall not be limited to the above-described embodiment and may be modified in various ways. For example, in the above-described embodiment, a measurement region of a subject is irradiated with light to detect diffused light from the measurement region, a light absorption coefficient distribution inside the measurement region is computed on the basis of the detected signal, and a reconstructed image for the interior of the measurement region is generated. However, the present invention is not limited to a bioinstrumentation apparatus or an image generating method in which light is used, but can be applied to a bioinstrumentation apparatus and an image generating method in which radiation rays and sonic waves are used.

That is, the bioinstrumentation apparatus of the present invention may be provided with an irradiation unit irradiating a measurement region of a subject with radiation rays or sonic waves, a detection unit detecting the radiation rays or the sonic waves diffused from the measurement region, and a computing unit computing a radiation ray or sonic wave absorption coefficient distribution inside the measurement region on the basis of an output signal from the detection unit to generate a reconstructed image for the interior of the measurement region. In this case, the computing unit preferably generates the reconstructed image by the method similar to that of the above-described embodiment. Further, the image generating method of the present invention may be a method of irradiating a measurement region of a subject with radiation rays or sonic waves, detecting the radiation rays or the sonic waves diffused from the measurement region, and computing a radiation ray or sonic wave absorption coefficient distribution inside the measurement region on the basis of the detected signal to generate a reconstructed image for the interior of the measurement region by the method similar to that of the above-described embodiment. Here, the radiation rays include short-wavelength electromagnetic waves, for example, X-rays, γ rays and microwaves, and the sonic waves include waves, for example, ultrasonic waves.

The first bioinstrumentation apparatus of the above-described embodiment is provided with a light irradiation unit which irradiates a measurement region of a subject with light, a light detection unit which detects diffused light from the measurement region, and a computing unit which computes a light absorption coefficient distribution inside the measurement region on the basis of an output signal from the light detection unit to generate a reconstructed image of the interior of the measurement region, in which the computing unit calculates J coefficients $w_j$ which are set for respective pixels of the reconstructed image and more than 0 and not more than 1 (where an index j is an integer from 1 to J, and J is the number of pixels of the reconstructed image), and carries out successive approximation computation by means of the above-described iterative formula (1), thereby generating the reconstructed image.

Further, the second bioinstrumentation apparatus of the above-described embodiment is provided with an irradiation unit which irradiates a measurement region of a subject with radiation rays or sonic waves, a detection unit which detects the radiation rays or the sonic waves diffused from the measurement region, and a computing unit which computes a radiation ray or sonic wave absorption coefficient distribution inside the measurement region on the basis of an output signal from the detection unit to generate a reconstructed image of the interior of the measurement region, in which the computing unit calculates J coefficients $w_j$ which are set for respective pixels of the reconstructed image and more than 0 and not more than 1 (where an index j is an integer from 1 to J, and J is the number of pixels of the reconstructed image), and carries out successive approximation computation by means of the above-described iterative formula (1), thereby generating the reconstructed image. In this configuration, the radiation rays include short-wavelength electromagnetic waves, for example, X-rays, γ rays and microwaves, and the sonic waves include waves, for example, ultrasonic waves.

The bioinstrumentation apparatus may also be configured so that the computing unit determines a convergence rate of a partial region which is slowest in convergence rate on iterative computation carried out N times (lowest convergence rate) $C_N$ among a plurality of partial regions in which the reconstructed image is divided and each of which contains a plurality of pixels, provides M values $v_m$ which meet a condition of $0<v_m<1$ (where m is an integer from 1 to M), carries out iterative computation N times for each m from 1 to M by means of the above-described iterative formula (2) to calculate J pixel values $x_1^{(N)}$ to $x_J^{(N)}$ of each pixel, and sets a value $v_m$, when the convergence rate of each partial region obtained from the pixel value $x_1^{(N)}$ to $x_J^{(N)}$ is substantially in agreement with the lowest convergence rate $C_N$, as the coefficient $w_j$ for the plurality of pixels contained in the partial region. It is, thereby, possible to obtain the above-described effects more favorably.

The bioinstrumentation apparatus may also be configured so that the computing unit sets the coefficient $w_j$ of the partial region, which is slowest in convergence rate on iterative computation carried out N times, as 1. It is, thereby, possible to obtain the above-described effects more favorably.

The first image generating method of the above-described embodiment is a method of irradiating a measurement region of a subject with light, detecting diffused light from the measurement region, and computing a light absorption coefficient distribution inside the measurement region on the basis of the detected signal to generate a reconstructed image of the interior of the measurement region, wherein the method calculates J coefficients $w_j$ which are set for respective pixels of the reconstructed image and more than 0 and not more than 1 (where an index j is an integer from 1 to J, and J is the number of pixels of the reconstructed image), and carries out successive approximation computation by means of the above-described iterative formula (3), thereby generating the reconstructed image.

Further, the second image generating method of the above-described embodiment is a method of irradiating a measurement region of a subject with radiation rays or sonic waves, detecting the radiation rays or the sonic waves diffused from the measurement region, and computing a radiation ray or sonic wave absorption coefficient distribution inside the measurement region on the basis of the detected signal to generate a reconstructed image of the interior of the measurement region, wherein the method calculates J coefficients $w_j$ which are set for respective pixels of the reconstructed image and more than 0 and not more than 1 (where an index j is an integer from 1 to J, and J is the number of pixels of the reconstructed image), and carries out successive approximation computation by means of the above-described iterative formula (3), thereby generating the reconstructed image. In this configuration, the radiation rays include short-wavelength electromagnetic waves, for example, X-rays, γ rays and microwaves, and the sonic waves include waves, for example, ultrasonic waves.

The image generating method may also be configured so that the method determines a convergence rate of a partial region which is slowest in convergence rate on iterative computation carried out N times (lowest convergence rate) $C_N$ among a plurality of partial regions in which the reconstructed image is divided and each of which contains a plurality of pixels, provides M values $v_m$ which meet a condition of $0<v_m<1$ (where m is an integer from 1 to M), carries out iterative computation N times for each m from 1 to M by means of the above-described iterative formula (4) to calculate J pixel values $x_1^{(N)}$ to $x_J^{(N)}$ of each pixel, and sets a value $v_m$, when the convergence rate of each partial region obtained from the pixel values $x_1^{(N)}$ to $x_j$ is substantially in agreement with the lowest convergence rate $C_N$, as the coefficient $w_j$ for the plurality of pixels contained in the partial region. It is, thereby, possible to obtain the above-described effects more favorably.

The image generating method may also be configured so that the method sets the coefficient $w_j$ of the partial region, which is slowest in convergence rate on iterative computation carried out N times, as 1. It is, thereby, possible to obtain the above-described effects more favorably.

Industrial Applicability

The present invention is usable as a bioinstrumentation apparatus and an image generating method capable of suppressing a difference in spatial resolution and noise characteristics depending on a position in a measurement region to generate an image which is uniform to a greater extent.

Reference Signs List

10—bioinstrumentation apparatus, 14—computing unit, 16—light emitting/detecting end, 22—light source, 24—optical switch, 26—light source optical fiber, 28—emission optical fiber, 30—photodetector, 32—shutter, 34—detection optical fiber, 36—signal processing circuit, 38—displaying unit.

The invention claimed is:

1. A bioinstrumentation apparatus comprising:
a light irradiation unit irradiating a measurement region of a subject with light;
a light detection unit detecting diffused light from the measurement region; and
a computing unit computing a light absorption coefficient distribution inside the measurement region on the basis of an output signal from the light detection unit to generate a reconstructed image for the interior of the measurement region, wherein
the computing unit calculates J coefficients $w_j$ which are set for every pixel of the reconstructed image and more than 0 and not more than 1 (where an index j is an integer from 1 to J, and J is the number of pixels of the reconstructed image), and carries out successive approximation computation by means of the following iterative formula $$x_j^{(k+1)} = x_j^{(k)} + w_j d_j^{(k)}$$

(where k is an integer from 1 to N, N is the number of times for carrying out iterative computation, $x_j^{(k)}$ is a pixel value of the jth pixel on the kth iterative computation, and $d_j^{(k)}$ is an update amount of the jth pixel on the kth iterative computation), thereby generating the reconstructed image.

2. The bioinstrumentation apparatus according to claim 1, wherein the computing unit
determines a convergence rate of a partial region which is slowest in convergence rate on iterative computation carried out N times (hereinafter referred to as a lowest convergence rate) $C_N$ among a plurality of partial regions in which the reconstructed image is divided and each of which contains a plurality of pixels,
provides M values $v_m$ which meet a condition of $0 < v_m < 1$ (where m is an integer from 1 to M),
carries out iterative computation N times for each m from 1 to M by means of the following iterative formula $$x_j^{(k+1)} = x_j^{(k)} + v_m d_j^{(k)}$$

to calculate J pixel values $x_1^{(N)}$ to $x_J^{(N)}$ of each pixel, and
sets a value $v_m$, when the convergence rate of each partial region obtained from the pixel values $x_1^{(N)}$ to $x_J^{(N)}$ is substantially in agreement with the lowest convergence rate $C_N$, as the coefficient $w_j$ for the plurality of pixels contained in the partial region.

3. The bioinstrumentation apparatus according to claim 2, wherein the computing unit sets the coefficient $w_j$ of the partial region, which is slowest in convergence rate on iterative computation carried out N times, as 1.

4. A bioinstrumentation apparatus comprising:
an irradiation unit irradiating a measurement region of a subject with radiation rays or sonic waves;
a detection unit detecting the radiation rays or the sonic waves diffused from the measurement region; and
a computing unit computing a radiation ray or sonic wave absorption coefficient distribution inside the measurement region on the basis of an output signal from the detection unit to generate a reconstructed image for the interior of the measurement region, wherein
the computing unit calculates J coefficients $w_j$ which are set for every pixel of the reconstructed image and more than 0 and not more than 1 (where an index j is an integer from 1 to J, and J is the number of pixels of the reconstructed image), and carries out successive approximation computation by means of the following iterative formula $$x_j^{(k+1)} = x_j^{(k)} + w_j d_j^{(k)}$$

(where k is an integer from 1 to N, N is the number of times for carrying out iterative computation, $x_j^{(k)}$ is a pixel value of the jth pixel on the kth iterative computation, and $d_j^{(k)}$ is an update amount of the jth pixel on the kth iterative computation), thereby generating the reconstructed image.

5. The bioinstrumentation apparatus according to claim 4, wherein the computing unit
determines a convergence rate of a partial region which is slowest in convergence rate on iterative computation carried out N times (hereinafter referred to as a lowest convergence rate) $C_N$ among a plurality of partial regions in which the reconstructed image is divided and each of which contains a plurality of pixels,
provides M values $v_m$ which meet a condition of $0 < v_m < 1$ (where m is an integer from 1 to M),
carries out iterative computation N times for each m from 1 to M by means of the following iterative formula $$x_j^{(k+1)} = x_j^{(k)} + v_m d_j^{(k)}$$

to calculate J pixel values $x_1^{(N)}$ to $x_J^{(N)}$ of each pixel, and
sets a value $v_m$, when the convergence rate of each partial region obtained from the pixel values $x_1^{(N)}$ to $x_J^{(N)}$ is substantially in agreement with the lowest convergence rate $C_N$, as the coefficient $w_j$ for the plurality of pixels contained in the partial region.

6. The bioinstrumentation apparatus according to claim 5, wherein the computing unit sets the coefficient $w_j$ of the partial region, which is slowest in convergence rate on iterative computation carried out N times, as 1.

7. An image generating method of irradiating a measurement region of a subject with light, detecting diffused light from the measurement region, and computing a light absorption coefficient distribution inside the measurement region on the basis of the detected signal to generate a reconstructed image for the interior of the measurement region, wherein
the method calculates J coefficients $w_j$ which are set for every pixel of the reconstructed image and more than 0 and not more than 1 (where an index j is an integer from 1 to J, and J is the number of pixels of the reconstructed image), and
carries out successive approximation computation by means of the following iterative formula $$x_j^{(k+1)} = x_j^{(k)} + w_j d_j^{(k)}$$

(where k is an integer from 1 to N, N is the number of times for carrying out iterative computation, $x_j^{(k)}$ is a pixel value of the jth pixel on the kth iterative computation, and $d_j^{(k)}$ is an update amount of the jth pixel on the kth iterative computation), thereby generating the reconstructed image.

8. The image generating method according to claim 7, wherein
the method determines a convergence rate of a partial region which is slowest in convergence rate on iterative computation carried out N times (hereinafter referred to as a lowest convergence rate) $C_N$ among a plurality of partial regions in which the reconstructed image is divided and each of which contains a plurality of pixels, provides M values $v_m$ which meet a condition of $0<v_m<1$ (where m is an integer from 1 to M), carries out iterative computation N times for each m from 1 to M by means of the following iterative formula $$x_j^{(k+1)}=x_j^{(k)}+v_m d_j^{(k)}$$

to calculate J pixel values $x_1^{(N)}$ to $x_J^{(N)}$ of each pixel, and sets a value $v_m$, when the convergence rate of each partial region obtained from the pixel values $x_1^{(N)}$ to $x_J^{(N)}$ is substantially in agreement with the lowest convergence rate $C_N$, as the coefficient $w_j$ for the plurality of pixels contained in the partial region.

9. The image generating method according to claim 8, wherein the method sets the coefficient $w_j$ of the partial region, which is slowest in convergence rate on iterative computation carried out N times, as 1.

10. An image generating method of irradiating a measurement region of a subject with radiation rays or sonic waves, detecting the radiation rays or the sonic waves diffused from the measurement region, computing a radiation ray or sonic wave absorption coefficient distribution inside the measurement region on the basis of the detected signal to generate a reconstructed image for the interior of the measurement region, wherein the method calculates J coefficients $w_j$ which are set for every pixel of the reconstructed image and more than 0 and not more than 1 (where an index j is an integer from 1 to J, and J is the number of pixels of the reconstructed image), and carries out successive approximation computation by means of the following iterative formula $$x_j^{(k+1)}=x_j^{(k)}+w_j d_j^{(k)}$$

(where k is an integer from 1 to N, N is the number of times for carrying out iterative computation, $x_j^{(k)}$ is a pixel value of the jth pixel on the kth iterative computation, and $d_j^{(k)}$ is an update amount of the jth pixel on the kth iterative computation), thereby generating the reconstructed image.

11. The image generating method according to claim 10, wherein the method determines a convergence rate of a partial region which is slowest in convergence rate on iterative computation carried out N times (hereinafter referred to as a lowest convergence rate) $C_N$ among a plurality of partial regions in which the reconstructed image is divided and each of which contains a plurality of pixels, provides M values $v_m$ which meet a condition of $0<v_m<1$ (where m is an integer from 1 to M), carries out iterative computation N times for each m from 1 to M by means of the following iterative formula $$x_j^{(k+1)}=x_j^{(k)}+v_m d_j^{(k)}$$

to calculate J pixel values $x_1^{(N)}$ to $x_J^{(N)}$ of each pixel, and sets a value $v_m$, when the convergence rate of each partial region obtained from the pixel values $x_1^{(N)}$ to $x_J^{(N)}$ is substantially in agreement with the lowest convergence rate $C_N$, as the coefficient $w_j$ for the plurality of pixels contained in the partial region.

12. The image generating method according to claim 11, wherein the method sets the coefficient $w_j$ of the partial region, which is slowest in convergence rate on iterative computation carried out N times, as 1.

* * * * *